United States Patent [19]
Gallo Mezo et al.

[11] Patent Number: 4,731,075
[45] Date of Patent: Mar. 15, 1988

[54] BICUSPATE CARDIAC-VALVE PROSTHESIS

[76] Inventors: José I. Gallo Mezo, Po Menéndez Pelayo 10; Manuel Carrion Alvarez, Avda. Los Castros 35, both of Santander; Blanca Ruiz, Paseo Migueletes 20, San Sebastian; Carlos Gomez Duran, Servicio de Cirugía Cardiovascular, Santander, all of Spain

[21] Appl. No.: 810,066

[22] Filed: Dec. 17, 1985

[30] Foreign Application Priority Data

Dec. 19, 1984 [ES] Spain ................................ 283.533[U]

[51] Int. Cl.[4] ................................................ A61F 2/24
[52] U.S. Cl. ....................................................... 623/2
[58] Field of Search ............................................. 623/2

[56] References Cited

U.S. PATENT DOCUMENTS

| | | | |
|---|---|---|---|
| 2,292,003 | 8/1942 | Yant et al. | 623/2 |
| 4,078,268 | 3/1978 | Possis | 623/2 |
| 4,339,831 | 7/1982 | Johnson | 623/2 |
| 4,373,216 | 2/1983 | Klawitter | 623/2 |
| 4,488,318 | 12/1984 | Kaster | 623/2 |
| 4,561,129 | 12/1985 | Arpesella | 623/2 |
| 4,597,767 | 7/1986 | Leukei | 623/2 |

Primary Examiner—Richard J. Apley
Assistant Examiner—James Prizant
Attorney, Agent, or Firm—Ladas & Parry

[57] ABSTRACT

A biscuspate cardiac valve prosthesis for use in human clinical medicine as a mitral valve graft. The valve has a support ring with an arched crosspiece containing apertures or a single longitudinal aperture along its length, joined at its ends to the lower portion of the support ring. Valve flaps are attached to both sides of the crosspiece, the opposite edges of the flaps being able to move freely during functioning of the valve. When the valve is closed, the flaps abut the inner surface of the support ring in a low dome profile.

8 Claims, 4 Drawing Figures

BICUSPATE CARDIAC-VALVE PROSTHESIS

This invention relates to a bicuspate cardiac-valve prosthesis of improved function over those of the prior art.

All attempts to date to make bicuspate (of two flaps or folds) cardiac-valve prostheses for use as mitral valve grafts in human clinical medicine have been unsuccessful, owing to technical difficulties in their construction and to poor hemodynamics achieved with these prostheses. Consequently, and even though the mitral valve in animals is bicuspate, it was preferred to construct a tricuspate (of three flaps) valve prosthesis for use as a substitute mitral valve in humans. To make this three-flap valve the hog was used as donor, and its aortic valve—fitted in a special manner—has been widely used throughout the world in human cardiac-valve surgery. This type of three-flap valve prosthesis offers better hemodynamics than was previously possible with two-flap models, but nevertheless its aperture is still insufficient and in many cases comes to be stenotic, creating problems for the bearer patient.

This invention teaches a new valve design improving the effective area of cardiac-valve prostheses employed in human clinical medicine.

The valve of this invention, comprising two valve flaps jointed to a central crosspiece in the valve prosthesis, has the following advantages and general characteristics:
  only two flaps are employed, instead of the three used until now;
  the flaps are anchored to an arched central crosspiece containing apertures;
  the valve flaps are domed or arch-shaped;
  the hemodynamic valve area is ample;
  the dead zones may be adequately washed to prevent the accumulation of clots.

The following is a purely illustrative and not in the least restrictive description of an embodiment of the subject matter of the invention, with reference to the accompanying drawings in which.

Figure 1:
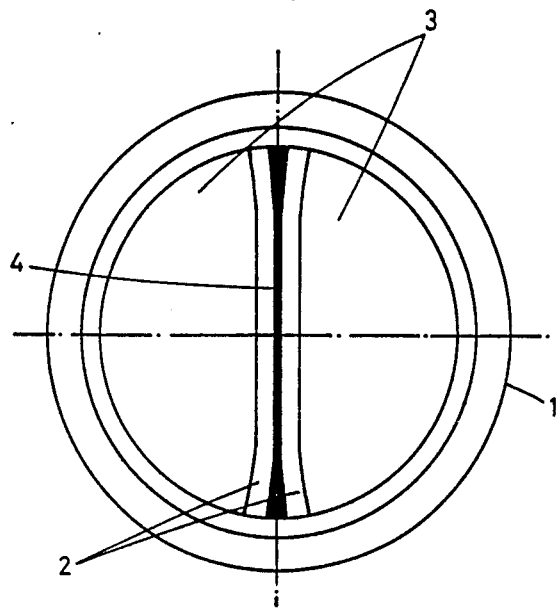
FIG. 1 is a top plan view of the valve.
Figure 2:
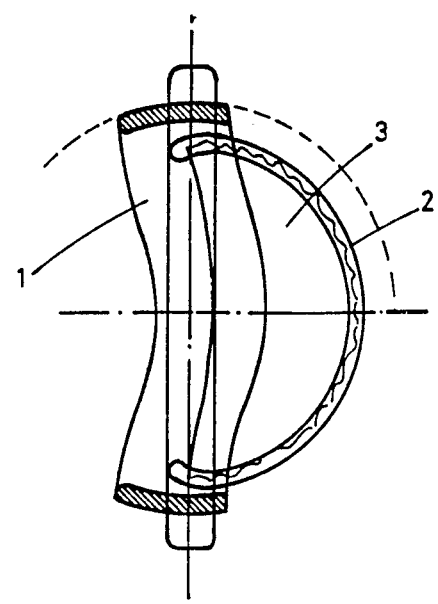
FIG. 2 is a diametrical view along the length of the longitudinal center line of the crosspiece anchor.
Figure 3:
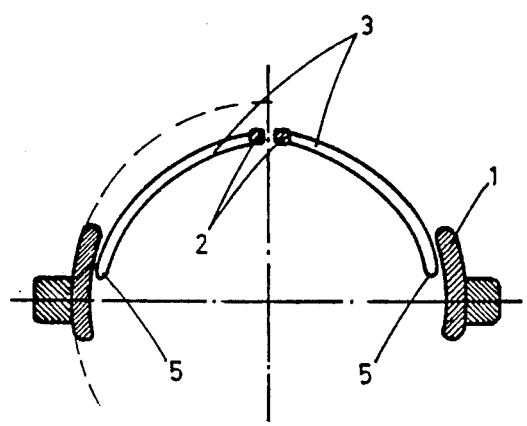
FIG. 3 is a diametrical view perpendicular to the view of FIG. 2.
Figure 4:
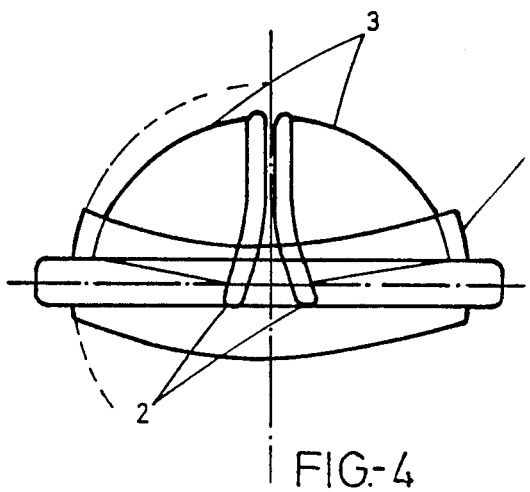
FIG. 4 is a side view of the valve.
Figure 5:
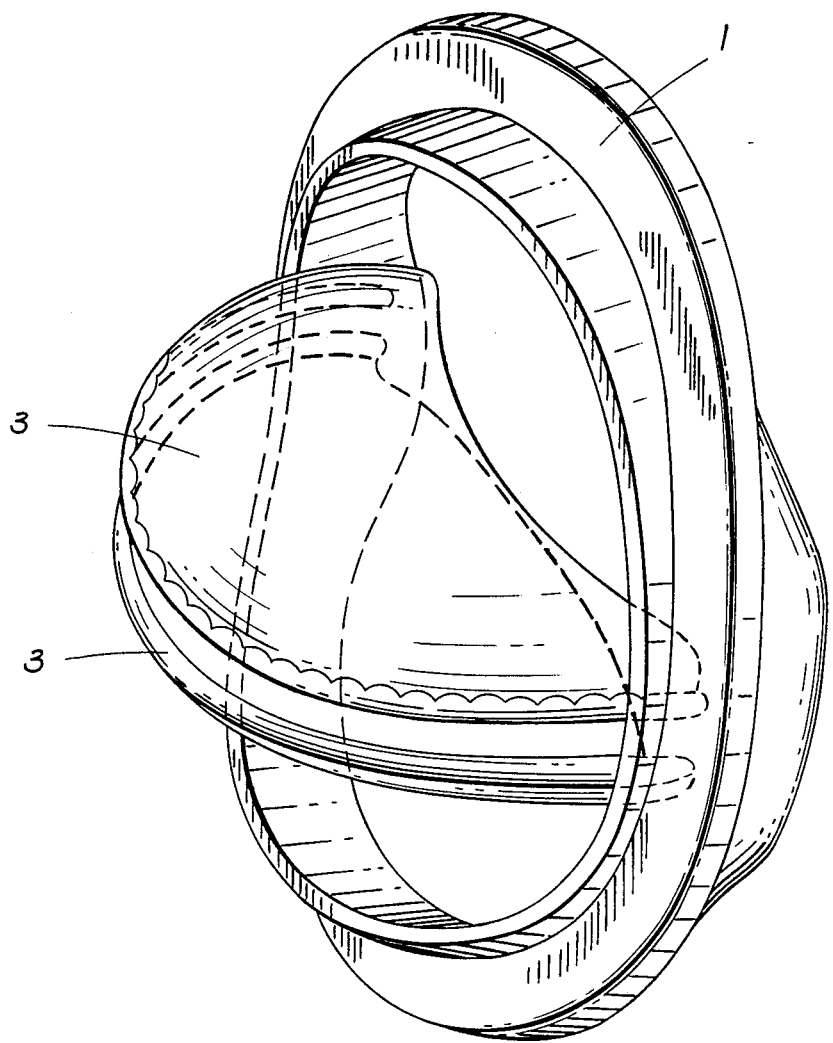
Figure 6:
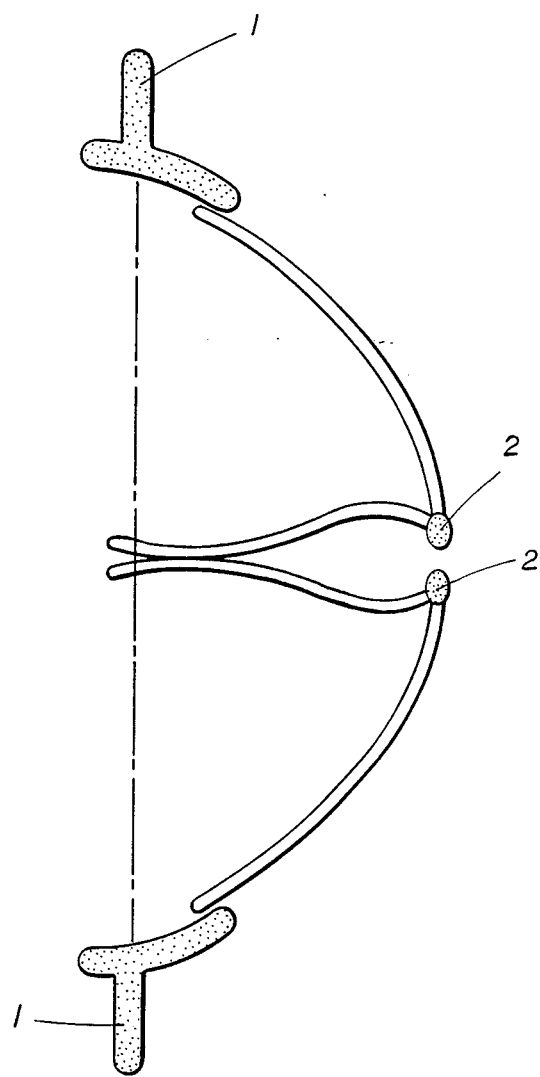

The prosthesis consists essentially of a low profile prosthetic valve ring 1, of circular shape and with an extended crosspiece or central post 2 as diameter of the valve ring. This arched central post 2 permits anchorage of the valve flaps 3. It contains several apertures, or else a continuous aperture 4, permitting the free passage of blood through them and the purpose of which shall be explained later. The apertures in this post can be located close to where it is joined with the circular ring, or in the case of a continuous aperture this can extend the length of the transversal post, with enlargement at the ends as is shown in FIGS. 1 and 4.

The ideal material for proper function of the described prosthesis would be the flaps of a porcine aortic valve. This in this invention two large flaps are used, not necessarily derived from the same animal and marked 3 in the drawings. Flaps of semisynthetic materials, such as biopolymers (polyurethanes), may also be used. These flaps are sewn on one edge to the central crosspiece or post 2 of the prosthesis, their opposite free edge 5 remaining in contact with the inner circumference of the valve ring 1 when the prosthesis is in closed position.

In valve prostheses currently on the market the valve flaps are anchored or sutured around the entire circumference of the valve ring, and thus there is no central anchoring crosspiece. In the present invention the place of implantation of the valve flaps is changed, by removing them from their natural position in the donor animal and resuturing them independently to the central crosspiece or post 1 of the prosthesis. In this manner the free edges of the valve flaps 3, which normally swing from the center to the periphery because the flaps are anchored in the circumference of the valve, swing in the opposite direction in the present invention (from the periphery to the center of the prosthesis) because the flaps are anchored in the center.

One of the possible problems of this special design of cardiac-valve prosthesis is that there may be zones in which inadequate "washing" of the blood can cause clot accumulation and the formation of abundant neointimae. The formation of neointimae or of clots would tend to develop on what would be the lower or ventricular surface of the valve, on the concavity of the central crosspiece 1 and of the cupolas formed by the valve flaps 3. This material accumulated in these zones would impede adequate function of the valve flaps and would come to cause malfunction of the valve.

To avoid this, a series of central apertures or a continuous aperture 4 permit free passage of the blood to both sides of the valve, providing adequate "washing" of these zones in which the blood can clot. To keep the passing of blood over these open zones from being hemolytic, the passage orifices should be lined with polyurethane.

In the function of the valve, the opening and closing movements of the valve flaps are always related in normal conditions with the pressure gradients on both sides of the valve, and with the flow of blood through the valve. The blood with materially "push" the valve flaps 3 to the sides, and the attainment of larger or smaller effective valve area will therefore depend on the quantity of blood which has to pass through the valve orifice at a given moment. In this valve the aperture of the valve flaps 3 is totally, independent of the flow, since the valve flaps "hang" from the central crosspiece 2 which support them. The moment there is a slight pressure gradient on both sides of the prosthesis, the flaps will open completely.

When the valve is closed, the valve flaps will abut the circumference of the support ring. To prevent fatigue of the tissue of which the valve flaps are made, and thus reduce their degeneration, it is recommended that the inner surface of the circumferential ring be lined with a silicone material or of biopolymers.

Although only one embodiment has been described as illustrative of the invention it is in no way limitative, and said invention must be considered limited only by the content of the following claims.

What is claimed:

1. A bicuspate cardiac-valve prosthesis for use in human clinical medicine as a mitral valve graft, comprising a support ring having an arched central or diametral crosspiece joined at its ends to the lower portion of said support ring, said central crosspiece being double edged, to both sides of which central crosspiece the inner edges of respective valve flaps are attached, while their opposite edges move freely during function of the apparatus and, when the valve is closed, abut against the inner surface of the support ring in a low, domed profile, and wherein the central crosspiece contains a series of apertures along its length to permit passage of a certain quantity of blood to prevent the formation of clots.

2. A prosthesis according to claim 1, wherein the apertures of the central crosspiece form a continuous longitudinal central aperture.

3. A prosthesis according to claim 1, wherein the valve flaps are sewn to the central crosspiece.

4. A prosthesis as in claim 1, wherein said crosspiece is integral to said support ring.

5. A prosthesis according to claim 2, wherein the longitudinal aperture is enlarged or widened at its ends.

6. A prosthesis as in claim 2, wherein said crosspiece is integral to said support ring.

7. A prosthesis as in claim 4, wherein said flaps are constructed from polyurethane, and the passages of said apertures are lined with polyurethane.

8. A prosthesis as in claim 6, wherein said flaps are constructed from polyurethane, and the passages of said apertures are lined with polyurethane.

* * * * *